US009382189B2

(12) United States Patent
Dubois et al.

(10) Patent No.: US 9,382,189 B2
(45) Date of Patent: Jul. 5, 2016

(54) SYNTHESIS OF A BRANCHED UNSATURATED COMPOUND BY MEANS OF CROSS METATHESIS

(71) Applicant: ARKEMA FRANCE, Colombes (FR)

(72) Inventors: Jean-Luc Dubois, Millery (FR); Jean-Luc Couturier, Lyons (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/766,588

(22) PCT Filed: Feb. 10, 2014

(86) PCT No.: PCT/FR2014/050248
§ 371 (c)(1),
(2) Date: Aug. 7, 2015

(87) PCT Pub. No.: WO2014/122411
PCT Pub. Date: Aug. 14, 2014

(65) Prior Publication Data
US 2015/0376108 A1 Dec. 31, 2015

(30) Foreign Application Priority Data
Feb. 8, 2013 (FR) .................... 13 51101

(51) Int. Cl.
C07C 67/347 (2006.01)
C07C 253/30 (2006.01)
C07C 51/353 (2006.01)
C07C 67/343 (2006.01)
C07C 253/00 (2006.01)
C07D 301/02 (2006.01)

(52) U.S. Cl.
CPC ............ C07C 67/347 (2013.01); C07C 51/353 (2013.01); C07C 67/343 (2013.01); C07C 253/00 (2013.01); C07C 253/30 (2013.01); C07D 301/02 (2013.01)

(58) Field of Classification Search
None
See application file for complete search history.

(56) References Cited

U.S. PATENT DOCUMENTS

| 6,946,567 | B2* | 9/2005 | Zhang | B01J 29/06 502/60 |
| 7,098,353 | B2* | 8/2006 | Zhang | C07C 67/333 502/77 |
| 7,166,766 | B1 | 1/2007 | Duhot et al. | |
| 8,377,661 | B2 | 2/2013 | Dubois | |
| 8,450,509 | B2 | 5/2013 | Dubois | |
| 8,642,792 | B2 | 2/2014 | Dubois et al. | |
| 8,697,401 | B2 | 4/2014 | Dubois | |
| 8,748,651 | B2 | 6/2014 | Dubois | |
| 8,835,661 | B2 | 9/2014 | Couturier et al. | |
| 8,884,041 | B2 | 11/2014 | Couturier et al. | |
| 8,933,285 | B2 | 1/2015 | Luetkens, Jr. et al. | |
| 8,940,923 | B2 | 1/2015 | Dubois | |
| 8,957,268 | B2 | 2/2015 | Cohen et al. | |
| 9,023,626 | B2 | 5/2015 | Dubois | |
| 9,096,490 | B2 | 8/2015 | Couturier et al. | |
| 2010/0168453 | A1 | 7/2010 | Dubois | |
| 2010/0196973 | A1 | 8/2010 | Dubois | |
| 2010/0216198 | A1 | 8/2010 | Dubois | |
| 2010/0305354 | A1 | 12/2010 | Dubois | |
| 2011/0104764 | A1 | 5/2011 | Dubois | |
| 2011/0105774 | A1 | 5/2011 | Dubois | |
| 2011/0113679 | A1 | 5/2011 | Cohen et al. | |
| 2011/0224454 | A1 | 9/2011 | Dubois | |
| 2011/0237850 | A1 | 9/2011 | Luetkens, Jr. et al. | |
| 2011/0300590 | A1 | 12/2011 | Dubois | |
| 2013/0116458 | A1 | 5/2013 | Couturier et al. | |
| 2013/0345388 | A1 | 12/2013 | Brandhorst et al. | |
| 2014/0155647 | A1 | 6/2014 | Dubois | |
| 2014/0163196 | A1 | 6/2014 | Couturier et al. | |
| 2014/0187808 | A1 | 7/2014 | Couturier et al. | |
| 2014/0194584 | A1 | 7/2014 | Dubois et al. | |
| 2014/0200358 | A1 | 7/2014 | Couturier et al. | |

FOREIGN PATENT DOCUMENTS

| EP | 1019512 | 7/2000 |
| FR | 2920768 | 3/2009 |
| FR | 2984309 | 6/2013 |
| WO | 2008104722 | 9/2008 |

(Continued)

OTHER PUBLICATIONS

Zhang, Z. C., et al., New Process for the production of branched-chain fatty acids, 2004, Journal of Surfactants and Detergents, vol. 7, No. 3, pp. 211-215.*
Carballeira et al., "First total synthesis and antileishmanial activity of (Z)-16-methyl-11-heptadecenoic acid, a new marine fatty acid from the sponge Dragmaxia undata." Chemistry and Physics of Lipids, Limerick, IR, 2010, vol. 164, No. 2, 113-117.
Bestmann et al., "Pheromone, VII. Synthese von 1-substituierten (Z)-9-Alkenen." Chemische Berichte, 1975, vol. 108, No. 11, 3582-3595.
Biermann et al., "Synthesis of alkyl-branched fatty acids." European Journal of Lipid Science and Technology, 2008, vol. 110, No. 9, 805-811.
International Search Report dated Jul. 2, 2014, issued in PCT/FR2014/050248 with English Translation.

(Continued)

Primary Examiner — Yate K Cutliff
(74) Attorney, Agent, or Firm — Miles & Stockbridge P.C.

(57) ABSTRACT

The invention relates to a method for the synthesis of a branched unsaturated fatty compound, said method comprising the metathesis, in the presence of a metathesis catalyst, of a linear unsaturated fatty compound and a branched olefin. The branched unsaturated fatty compound is used in particular for the production of at least one of the following products: dielectric fluids, specialty surfactants, emulsifiers, frictions agents, antistatic additives, antifogging additives, mould release agents, pigment dispersants, high-performance lubricants, waxes and wax emulsifiers, polymer conversion additives, PVC stabilizing agents, inks, resins, paints, varnishes, solvents, lipsticks, creams for the skin, deodorants, particularly stick deodorants, hair dyes, shampoos and other liquid soaps, shaving foam, laundry detergents, cleaning agents, fabric softeners, and mixtures of same.

25 Claims, No Drawings

(56) References Cited

FOREIGN PATENT DOCUMENTS

| | | |
|---|---|---|
| WO | 2008155506 | 12/2008 |
| WO | 2009047444 | 4/2009 |
| WO | 2009047445 | 4/2009 |
| WO | 2010004219 | 1/2010 |
| WO | 2010004220 | 1/2010 |
| WO | 2010055273 | 5/2010 |
| WO | 2010089512 | 12/2010 |
| WO | 2011138051 | 10/2011 |
| WO | 2012095575 | 7/2012 |
| WO | 2013017782 | 7/2013 |
| WO | 2013017786 | 7/2013 |
| WO | 2013030481 | 7/2013 |
| WO | 2014106723 | 7/2014 |
| WO | 2014106724 | 7/2014 |
| WO | 2014106766 | 7/2014 |
| WO | 2014122410 | 8/2014 |
| WO | 2014122412 | 8/2014 |
| WO | 2014147337 | 9/2014 |

OTHER PUBLICATIONS

French Search Report dated Oct. 16, 2013, issued in FA 776462/FA 1351101.

Zhang et al., Novel Process to Produce Branched Fatty Acid/Ester for Biodiesel and New Surfactant Applications, the Proceedings of the 3rd International Conference on Functional Molecules, p. 343-346, 2005.

Malchev, Plant-Oil-Based Lubricants, Dept. of Plant Agriculture, Ontario Agriculture College, University of Guelph.

Schaverien et al., A Well-Characterized, Highly Active, Lewis Acid Free Olefin Metathesis Catalyst, J. Am. Chem. Soc., 1986, 108, pp. 2771-2773.

Scholl et al., Synthesis and Activity of a New Generation of Ruthenium-Based Olefin Metathesis Catalysts Coordinated with 1,3-Dimesityl-4,5-dihydroimidazol-2-ylidene Ligands§, Organic Letters, 1999, 1:6, pp. 953-956.

Schwab et al., A Series of Well-Defined Metathesis Catalysts-Synthesiss of [RuCl2(=CHR1)(pr3)2| and Its Reactions, Angew. Chem. Int. Ed. Engl., 1995, 34:18, pp. 2039-2041.

Couturier et al., A cyclometalated Aryloxy(chloro)neopentylidene-tungsten Complex: A highly Active and Stereoselective Catalyst for the Metathesis of cis- and tran-2-Pentene, Norbomene, 1-Methylnorbomen, and Ethy Oleate, Angew. Chem. Int. Ed. Engl., 1992 31:2, pp. 628-631.

* cited by examiner

SYNTHESIS OF A BRANCHED UNSATURATED COMPOUND BY MEANS OF CROSS METATHESIS

FIELD OF THE INVENTION

The subject of the invention is a process for synthesizing an unsaturated and branched fatty acid, ester or nitrile compound using at least one metathesis reaction.

For the purposes of the invention:
- the term "acid, ester or nitrile compound": means an aliphatic compound bearing at least one acid, ester or nitrile end function;
- the term "fatty compound": means an aliphatic compound whose longest main chain comprises from 8 to 36 carbon atoms, preferably from 8 to 26, preferably from 10 to 24 carbon atoms;
- the term "unsaturated compound": means an aliphatic compound which comprises one or more carbon-carbon double bonds;
- the term "branched compound": means an aliphatic compound with a linear main chain comprising at least one other carbon-based chain (or "branching") with a number of carbons in the range from 1 to 11, preferably from 1 to 10, preferably from 1 to 5, on at least one of the carbons of the main chain;

Further, the abbreviation "branched unsaturated fatty compound" is used to denote any "branched unsaturated fatty acid, ester or nitrile compound" according to the invention.

TECHNICAL BACKGROUND

Branched fatty acids exist in nature (http://www.cyberlipid.org/cyberlip/home0001.htm), but are extremely rare, sparingly commercially available and particularly expensive. To illustrate the rarity of these products, it may be noted that the price of products of this category is much higher than that of the unbranched products, for example in the catalog from the Aldrich company http://www.sigmaaldrich.com/catalog/product/sigma/m6281?lang=fr&region=FR.

Various processes for synthesizing these branched unsaturated fatty acids are described in the literature. Mention may be made of the isomerization of fatty acids under heterogeneous catalysis; however, this process leads to a broad distribution of various branched fatty acids. Mention may be made in this respect of the article by U. Biermann et al. in *Eur. J. Lipid Sci.* Technology, entitled *Synthesis of alkyl branched fatty acids* 2008, 110, 805-811 and that of Zhang et al., published in The proceedings of the 3rd International Conference on Functional Molecules, entitled *Novel Process to Produce Branched Fatty Acid/Ester for Biodiesel and New Surfactant.*

Various other methods such as the alkylation of olefins, hydroformylation and hydrogenation processes, fatty acid dimerization processes, Friedel-Crafts reactions, reactions involving formaldehyde (ENE reaction) and radical additions have been studied, as evidenced by the article from Ivan Malchev entitled *Plant Oil based Lubricants* available from the Department of Plant Agriculture, Ontario Agriculture College, University of Guelph, 50 Stone Road W., Guelph, Ontario, Canada N1G 2W1 and downloaded from the Internet at http://ebookbrowse.com/i-malchev-pdf-d92064738 and http://www.pdfio.com/k-1103149.html. However, it should be noted that, globally, none of these methods is entirely satisfactory. The products obtained by catalytic isomerization are mixtures of isomers; the products obtained by hydroformylation are saturated and certain cold properties are thus lost; the addition products, especially from radical addition, are mixtures, and it is not possible to obtain a quite specific product.

Another recent approach, described especially in patent EP 1 019 512, consists in identifying the genes in plants that lead to branched acids and in transferring them into microorganisms to make them produce specific acids. However, this method is merely in its infancy.

Branched compounds are distinguished from linear compounds by lower melting points and this property offers certain industrial openings. Mention may be made in this respect of isostearic acid, which is a commercial product, obtained as a by-product of the process for dimerizing oleic acid by catalysis with montmorillonite. The influence of isostearic acid on the spreading, viscosity and oxidation-stability and hydrolysis-stability properties of the products finds applications in the fields of cosmetics and lubrication (see the article by Biermann et al. cited previously).

In general, the strategy adopted by industrialists in the oleochemistry sector who have no access to branched compounds in sufficient concentration is to use as an alternative unsaturated compounds, which, themselves also, offer lower melting points than those of the corresponding saturated linear compounds. However, the unsaturated compounds are also less stable, and are sensitive to oxidation.

There is thus a real need to develop a quick and simple process (comprising the fewest possible steps) for synthesizing branched fatty compounds, especially branched unsaturated fatty acids.

In a known manner, cross metathesis consists in reacting, in the presence of a metathesis catalyst, two unsaturated molecules according to the following schematic reaction process:

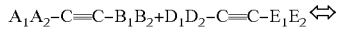

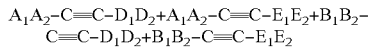

(cross metathesis), and

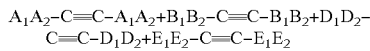

(homometathesis)

Cross metathesis is used for the purpose of synthesizing a target product, for example $A_1A_2-C\equiv C-D_1D_2$ in the above equation, but which will be accompanied, where appropriate, by the other three possible compounds derived from the cross metathesis of the same two reagents, and also certain compounds derived from the homometathesis of each reagent, this reaction accompanying the main reaction.

The use of metathesis was described by the company Elevance for the manufacture of fuel bases, especially aircraft fuels, from plant oils. Thus, patents US 2011/0113679 and US 2011/0237850 describe the reaction between a natural plant oil and a mixture of light olefins, leading, after additional treatment, to a mixture of compounds in which the number of carbon atoms is variable, multiple and uncontrolled, and whose properties in terms of energy density and flash point are suitable for the manufacture of fuels. Nevertheless, this type of mixture is not suitable for applications that are more stringent especially in terms of purity. Furthermore, the process described in each of these documents does not make it possible economically to manufacture compounds with a low melting point, i.e. with a melting point (m.p.) below 0° C., preferably below −20° C., even more preferably below −30° C.

The present invention is directed, on the contrary, toward providing a process in which the selectivity, the purity and thus the physicochemical properties of the branched unsaturated fatty compound are controlled, to be able to use it in high-performance technical applications, such as dielectric fluids, specialty surfactants, emulsifiers, friction agents, antistatic additives, antifogging additives, mold-release agents, pigment dispersants, high-performance lubricants, waxes and wax emulsifiers, polymer transformation additives, PVC stabilizers, inks, resins, paints, varnishes, solvents, lipsticks, skin creams, deodorants, especially in stick form, hair dyes, shampoos and other liquid soaps, shaving foams, detergents, cleaning agents, textile softeners, etc.

The Applicant has now found a means for making branched unsaturated compounds readily available, via a process using, under certain conditions, a cross metathesis reaction between at least two reagents selected according to the invention and making it possible more especially to target the synthesis of branched unsaturated fatty acid, ester or nitrile compounds. Unexpectedly, the process according to the invention promotes the synthesis of the target product, i.e. the synthesis of a branched unsaturated fatty compound in a yield of at least 70%, which is compatible with industrial applications.

SUMMARY OF THE INVENTION

The subject of the present invention is thus a process for synthesizing a branched unsaturated fatty acid, ester or nitrile compound that is perfectly targeted by using selected reagents in a cross metathesis reaction.

In particular, a subject of the invention is a process for synthesizing a branched unsaturated fatty compound of formula III: A-CH=CB'—B in which:

A is a radical consisting of an linear alkyl chain, comprising from 1 to 20 carbon atoms and comprising an acid, ester (of a monoalcohol or of a polyol) or nitrile end function, the linear alkyl chain being optionally unsaturated, B' is H or an alkyl chain comprising from 1 to 10 carbon atoms, and B is:
  if B' is an alkyl chain, B is an alkyl chain comprising from 1 to 11 carbon atoms, the alkyl chain being optionally branched,
  if B' is H, B is an alkyl chain comprising from 3 to 11 carbon atoms bearing at least one branched alkyl radical of formula $C_nH_{2n+1}$ with n in the range from 1 to 5, said process comprising metathesis in the presence of a metathesis catalyst between:
  on the one hand, a linear unsaturated fatty compound of formula I:

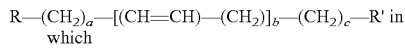

R—(CH$_2$)$_a$—[(CH=CH)—(CH$_2$)]$_b$—(CH$_2$)$_c$—R' in which

R' is a radical —COOH, —COOR$_1$ or —CN, R$_1$ being a monoalcohol or a polyol residue, such as diol or triol, R is H or an acid, monoalcohol ester or nitrile function, and a, b, c are integers such that $0 \leq a \leq 11$; $1 \leq b \leq 6$; $2 \leq c \leq 12$, the sum $a+3*b+c+1$ being in the range from 8 to 36, preferably from 8 to 24, preferably from 10 to 22 and even more preferably from 10 to 18; and
  on the other hand, a branched olefin II comprising from 4 to 23 carbon atoms, in which the main chain comprises at least one "branching" (or "alkyl radical") of formula $C_nH_{2n+1}$ with n in the range from 1 to 5 when (in formula III) B' is H.

DESCRIPTION OF EMBODIMENTS OF THE INVENTION

The invention is now described in greater detail and in a nonlimiting manner in the description which follows.

The linear unsaturated fatty compound I (occasionally also referred to as the "fatty molecule" in the present description) that may be used in the process of the invention is advantageously chosen from: monounsaturated or polyunsaturated fatty acids and fatty acid esters, and nitrile derivatives thereof, derived from plants or animal material, including the mono-, di- and triglycerides from which they are derived. Examples that may be mentioned include acids and acid esters chosen from the following acids: oleic, petroselinic, linoleic, ricinoleic, gadoleic, gondoic, vaccenic, linolenic, palmitoleic, erucic, nervonic, etc., the triglycerides from which they are derived, and mixtures thereof.

The unsaturated fatty compounds that may be used in the process of the invention also comprise the derivatives obtained by chemical transformation of the preceding molecules, such as the nitriles obtained by nitrilation of the ester or acid function. The unsaturated fatty compounds also comprise difunctional molecules bearing acid, ester or nitrile functions at each end of the molecule (in general two identical functions), and also the mono-, di- and triglycerides themselves optionally subjected to a prior chemical reaction, such as methanolysis, ethanolysis or metathesis with a light C2-C4 olefin.

In particular, the unsaturated fatty compounds may be derived from a chemical transformation of the fatty acids/esters/triglycerides mentioned above, for example via a cross metathesis of these compounds with a light olefin, ethylene, propylene or butenes, leading to functional molecules comprising from 8 to 36, preferably from 8 to 26, preferably from 8 to 24, preferably from 10 to 22 and even more preferably from 10 to 18 carbon atoms, and preferably ω, ω-1 or ω-2 unsaturated, which are suited to the metathesis reaction with the branched olefin II.

Preferably, the metathesis process of the invention is performed starting with an unsaturated fatty compound comprising a function, and preferably only one function, of monoalcohol ester, polyol ester or nitrile type. As described previously, the main sources of these compounds are natural oils or fats of animal or plant origin, including algae, from which may be extracted the triglycerides, and thus the constituent elements thereof.

The unsaturated fatty esters of monoalcohols are obtained, for example, via the action of a light alcohol, preferably methanol or ethanol, on the triglyceride. Thus, according to an advantageous embodiment of the process of the invention, a monoalcohol ester obtained by methanolysis or ethanolysis of a triglyceride is subjected to a cross metathesis reaction with a branched olefin.

The fatty esters of polyols generally comprise triglycerides extracted from plant oils, animal oils or fats, or originating from microalgae. These fatty esters are, prior to the metathesis with the branched olefin, subjected to a preliminary step of cross metathesis with one (or more) light olefin(s), ethylene, propylene or 1-butene or 2-butene, or 2-pentene, 2-hexene or 3-hexene, leading to the formation of unsaturated fatty esters bearing a double bond located close to the end of the alkyl chain (preferably ω, ω-1 or ω-2 unsaturated esters). A mixture of these light olefins may be used for this preliminary step. This preliminary step makes it possible to improve the performance of the cross metathesis with the branched olefin by virtue of the formation, during this reaction, of gaseous light olefins whose extraction from the reaction medium makes it possible to shift the metathesis reaction equilibrium.

Unsaturated fatty nitriles are generally obtained from the corresponding fatty acids or esters via the action of ammonia followed by dehydration of the compound, ammonium salt or amide, formed according to well-known reaction mechanisms.

In one implementation variant of the process of the invention, compound I is a diester or a dinitrile (for example of C18 or C20) obtained either by homometathesis of the ester or nitrile, main product of the homometathesis, or during a cross metathesis reaction in which the diester or the dinitrile is formed as coproduct. In this case, the metathesis reaction according to the process of the invention generates at least one branched compound and a compound which is a shorter ester or nitrile, which may be used again for other applications including a metathesis step.

The branched olefin II used for the metathesis reaction preferably contains at least 5 carbon atoms, more preferably at least 6 carbon atoms, even more preferably at least 7 carbon atoms, or better still at least 8 carbon atoms. The olefin preferably comprises from 7 to 12 and preferably from 8 to 12 carbon atoms in total.

The olefin used for the metathesis reaction is either monounsaturated or polyunsaturated. In the latter case, the double bonds are preferably non-conjugated. The reason for this is that the presence of conjugations tends to deactivate the metathesis catalyst.

The olefin is preferably monounsaturated. Specifically, when polyunsaturated olefins are used, an overconsumption of catalyst and of olefins is observed, and it thus becomes necessary to work at low conversion in order to limit the losses of products, which complicates the process.

Advantageously, the branched olefin II is of formula: $R_0R_0'C$═$CBB'$ in which:

B' is H or an alkyl chain comprising from 1 to 10 carbon atoms, and
  if B' is an alkyl chain, B is an alkyl chain comprising from 1 to 11 carbon atoms, the alkyl chain being optionally branched,
  if B' is H, B is an alkyl chain comprising from 3 to 11 carbon atoms including at least one carbon atom bearing an alkyl radical of formula $C_nH_{2n+1}$ with n in the range from 1 to 5, and
$R'_0$ is H or an alkyl chain comprising from 1 to 10 carbon atoms, and
  if $R'_0$ is H, $R_0$ is H, $CH_3$, $C_2H_5$ or an alkyl chain comprising from 3 to 11 carbon atoms including at least one carbon atom bearing an alkyl radical of formula $C_nH_{2n+1}$ with n in the range from 1 to 5, and
  if $R'_0$ is an alkyl chain, $R_0$ is H or an alkyl chain comprising from 1 to 11 carbon atoms, the alkyl chain being optionally branched.

According to an advantageous embodiment of the process of the invention, —B is an alkyl chain of formula —$(CR_2R_3)_m$—$CH_3$ in which $R_2$ and $R_3$ correspond to the definitions given below. The position of the —$CH_3$ group at the end of this alkyl chain B (opposite the double bond of formula II) is denoted in the present description by "ω", irrespective of the number of carbon atoms m connecting it to the double bond.

Advantageously, —$R_0$ is an alkyl chain of formula —$(CR_2'R_3')_p$—$CH_3$ in which $R_2'$ and $R_3'$ correspond to the definitions given below for $R_2$ and $R_3$. Similarly, the position of the —$CH_3$ group at the end of the chain $R_0$ (opposite the double bond of formula II) is also denoted by "ω" in the present description of the invention.

According to a preferred embodiment of the process of the invention, in formula II of the olefin, B' is H and —B is of formula —$(CR_2R_3)_m$—$CH_3$ in which $R_2$ and $R_3$, which may be identical or different, are either H or a saturated alkyl radical comprising from 1 to 5 carbon atoms, the radicals $R_2$, on the one hand, and the radicals $R_3$, on the other hand, linked to the carbon atoms of the chain being identical to or different from each other, and at least one of the radicals $R_2$ and $R_3$ being a saturated alkyl radical, said at least one carbon bearing said radical being in the chain preferably in position ω-i, i being >1 (i is an integer strictly greater than 1), especially in position ω-2, ω-3, etc.

Advantageously, the branching(s) of the olefin is(are) of the olefin preferably located closer to the double bond C═C than the end of the chain which bears said branching(s). Specifically, it turns out that the melting point of the branched unsaturated fatty compounds thus obtained via the process of the invention is proportionately lower the further the position of a branching from the end of the chain and thus the closer it is to the double bond C═C.

According to a preferred embodiment of the process of the invention, each carbon atom of the double bond of formula II: $R_0R_0'C$═$CBB'$ bears only one alkyl chain. In other words, and preferably, the alkyl radicals of the branching of the olefin are not linked to a carbon atom of a double bond. Under these conditions, the metathesis reaction proceeds better, and better conversion and less consumption of catalyst are observed.

Furthermore, in the olefin II used, the carbon atoms bearing the double bond are preferably linked on one side of the double bond to a chain of not more than 2 other carbon atoms and are therefore preferably of the 1-alkene, 2-alkene or 3-alkene type, which also facilitates the cross metathesis reaction according to the invention. The coproduct formed in this particular case of the process of the invention is a "light" product comprising less than 8 carbons, preferably less than 7, or even less than 5 or better still less than 3 carbons, which is easy to extract from the reaction medium, thus making it possible to advance the metathesis reaction more quickly.

Depending on the degree of purity and the degree of control of the physicochemical properties of the target compound III, a branched olefin in accordance with the above definition may be used either alone (and preferably as pure as possible) or as a mixture with one or more other olefins which may or may not be in accordance with the above definition. By way of example, the branched olefin may be used in the form of a mixture with one or more linear olefins. Examples of mixtures of olefins that are suitable for the process of the invention and commercially available are especially propylene and butene oligomers or mixtures of olefins derived from petroleum fractions, for example light petroleum spirits.

Table 1 below gives examples of preferred olefins in which the double bond does not bear any branching. Only olefins of 5 to 9 carbon atoms are illustrated therein, so as not to unnecessarily emburden the description. Needless to say, the definition of the olefin is not limited to these examples.

The first column indicates the length of the main linear chain (the longest) of the olefin, the second indicates the position of the double bond, the following columns indicate the positions of the methyl, ethyl and propyl groups, and the final column indicates the total number of carbon atoms in the olefin.

TABLE 1

| Chain Length | C═C Position | Methyl Position | | Ethyl | Propyl | Number of Carbons |
|---|---|---|---|---|---|---|
| 4 | 1 | 3 | | | | 5 |
| 4 | 1 | 3 | 3 | | | 6 |
| 5 | 1 | 4 | | | | 6 |
| 5 | 1 | 3 | | | | 6 |
| 5 | 2 | 4 | | | | 6 |
| 5 | 1 | 4 | 4 | | | 7 |

TABLE 1-continued

| Chain Length | C=C Position | Methyl Position | | | Ethyl | Propyl | Number of Carbons |
|---|---|---|---|---|---|---|---|
| 5 | 1 | 3 | 3 | | | | 7 |
| 5 | 1 | | | | 3 | | 7 |
| 5 | 1 | 3 | 4 | | | | 7 |
| 5 | 2 | 4 | 4 | | | | 7 |
| 6 | 1 | 5 | | | | | 7 |
| 6 | 1 | 4 | | | | | 7 |
| 6 | 1 | 3 | | | | | 7 |
| 6 | 2 | 4 | | | | | 7 |
| 6 | 2 | 5 | | | | | 7 |
| 6 | 3 | 2 | | | | | 7 |
| 5 | 1 | 4 | | | 3 | | 8 |
| 5 | 1 | 3 | 4 | 4 | | | 8 |
| 5 | 1 | 3 | | | 3 | | 8 |
| 5 | 1 | 3 | 3 | 4 | | | 8 |
| 6 | 1 | 3 | 3 | | | | 8 |
| 6 | 1 | 3 | 4 | | | | 8 |
| 6 | 1 | 3 | 5 | | | | 8 |
| 6 | 1 | 4 | 4 | | | | 8 |
| 6 | 1 | 4 | 5 | | | | 8 |
| 6 | 1 | 5 | 5 | | | | 8 |
| 6 | 1 | | | | 3 | | 8 |
| 6 | 1 | | | | 4 | | 8 |
| 6 | 2 | 4 | 4 | | | | 8 |
| 6 | 2 | 4 | 5 | | | | 8 |
| 6 | 2 | 5 | 5 | | | | 8 |
| 6 | 2 | | | | 4 | | 8 |
| 6 | 3 | 2 | 2 | | | | 8 |
| 6 | 3 | 2 | 5 | | | | 8 |
| 7 | 1 | 3 | | | | | 8 |
| 7 | 1 | 4 | | | | | 8 |
| 7 | 1 | 5 | | | | | 8 |
| 7 | 1 | 6 | | | | | 8 |
| 7 | 2 | 4 | | | | | 8 |
| 7 | 2 | 5 | | | | | 8 |
| 7 | 2 | 6 | | | | | 8 |
| 7 | 3 | 2 | | | | | 8 |
| 7 | 3 | 5 | | | | | 8 |
| 7 | 3 | 6 | | | | | 8 |
| 5 | 1 | 3 | 3 | 4 | 4 | | 9 |
| 5 | 1 | 3 | | 4 | | 3 | 9 |
| 6 | 1 | 3 | 3 | 4 | | | 9 |
| 6 | 1 | 3 | 3 | 5 | | | 9 |
| 6 | 1 | 3 | 4 | 5 | | | 9 |
| 6 | 1 | 3 | 4 | 4 | | | 9 |
| 6 | 1 | 3 | 5 | 5 | | | 9 |
| 6 | 1 | 4 | 4 | 5 | | | 9 |
| 6 | 1 | 4 | 5 | 5 | | | 9 |
| 6 | 1 | 3 | | | 3 | | 9 |
| 6 | 1 | 3 | | | 4 | | 9 |
| 6 | 1 | 4 | | | 3 | | 9 |
| 6 | 1 | 4 | | | 4 | | 9 |
| 6 | 1 | 5 | | | 3 | | 9 |
| 6 | 1 | 5 | | | 4 | | 9 |
| 6 | 1 | | | | | 3 | 9 |
| 6 | 2 | 4 | 5 | 5 | | | 9 |
| 6 | 2 | 4 | 4 | 5 | | | 9 |
| 6 | 2 | 4 | | | 4 | | 9 |
| 6 | 3 | 2 | 2 | 5 | | | 9 |
| 7 | 1 | 3 | 3 | | | | 9 |
| 7 | 1 | 3 | 4 | | | | 9 |
| 7 | 1 | 3 | 5 | | | | 9 |
| 7 | 1 | 3 | 6 | | | | 9 |
| 7 | 1 | 4 | 4 | | | | 9 |
| 7 | 1 | 4 | 5 | | | | 9 |
| 7 | 1 | 4 | 6 | | | | 9 |
| 7 | 1 | | | | 3 | | 9 |
| 7 | 1 | | | | 4 | | 9 |
| 7 | 1 | | | | 5 | | 9 |
| 7 | 2 | 4 | 4 | | | | 9 |
| 7 | 2 | 4 | 5 | | | | 9 |
| 7 | 2 | 4 | 6 | | | | 9 |
| 7 | 2 | 5 | 5 | | | | 9 |
| 7 | 2 | 5 | 6 | | | | 9 |
| 7 | 2 | 6 | 6 | | | | 9 |
| 7 | 2 | | | | 4 | | 9 |
| 7 | 2 | | | | 5 | | 9 |
| 7 | 3 | 2 | 2 | | | | 9 |
| 7 | 3 | 2 | 5 | | | | 9 |
| 7 | 3 | 2 | 6 | | | | 9 |
| 7 | 3 | 5 | 5 | | | | 9 |
| 7 | 3 | 5 | 6 | | | | 9 |
| 7 | 3 | 6 | 6 | | | | 9 |
| 8 | 1 | 3 | | | | | 9 |
| 8 | 1 | 4 | | | | | 9 |
| 8 | 1 | 5 | | | | | 9 |
| 8 | 1 | 6 | | | | | 9 |
| 8 | 1 | 7 | | | | | 9 |
| 8 | 2 | 4 | | | | | 9 |
| 8 | 2 | 5 | | | | | 9 |
| 8 | 2 | 6 | | | | | 9 |
| 8 | 2 | 7 | | | | | 9 |
| 8 | 3 | 2 | | | | | 9 |
| 8 | 3 | 5 | | | | | 9 |
| 8 | 3 | 6 | | | | | 9 |
| 8 | 3 | 7 | | | | | 9 |
| 8 | 4 | 2 | | | | | 9 |
| 8 | 4 | 3 | | | | | 9 |

The cross metathesis reaction according to the process of the invention is performed in the presence of at least one metathesis catalyst.

Many metathesis catalysts exist, and they are well known. Mention may, for example, be made of the tungsten complexes developed by Schrock et al (*J. Am. Chem. Soc.* 108: 2771, 1986) or Basset et al. (*Angew. Chem., Ed. Engl.* 31:628, 1992). More recently, catalysts termed Grubbs catalysts have emerged (see Grubbs et al., Angew. Chem., Ed. Engl. 34:2039, 1995 and *Organic Letters* 1:953, 1999) which are ruthenium-benzylidene complexes operating in homogeneous catalysis. Other studies have been carried out in order to produce immobilized catalysts, i.e. catalysts of which the active ingredient is that of the homogeneous catalyst, in particular ruthenium-carbene complexes immobilized on an inactive support.

The process according to the invention advantageously uses a metathesis catalyst of ruthenium-carbene type.

The ruthenium-carbene catalysts are preferably chosen from charged or uncharged catalysts of general formula:

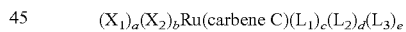

in which:
  a, b, c, d and e are integers, which may be identical or different, with a and b equal to 0, 1 or 2; c, d and e equal to 0, 1, 2, 3 or 4;
  $X_1$ and $X_2$, which may be identical or different, each represent a charged or uncharged and monochelating or polychelating ligand; by way of example, mention may be made of halides, sulfate, carbonate, carboxylates, alkoxides, phenolates, amides, tosylate, hexafluorophosphate, tetrafluoroborate, bis(triflyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and
  $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

The carbene C is represented by the general formula: $CR_1R_2$ for which $R_1$ and $R_2$ are groups which may be identical or different, such as hydrogen or any other functionalized or non-functionalized hydrocarbon-based group of saturated, unsaturated, cyclic, aromatic, branched and/or linear type. By way of examples, mention may be made of ruthenium alkylidene, benzylidene, benzylidene ether or cumylene complexes, such as vinylidenes Ru=C=CHR or allenylidenes Ru=C=C=$CR_1R_2$ or indenylidenes.

A functional group (making it possible to improve the retention of the ruthenium complex in an ionic liquid) can be grafted onto at least one of the ligands $X_1$, $X_2$, $L_1$, $L_2$, or onto the carbene C. This functional group may be charged or uncharged, such as preferably an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The metathesis catalyst can optionally be rendered heterogeneous on a support in order to facilitate the recovery/recycling thereof.

The cross metathesis catalysts of the process of the invention are preferably ruthenium carbenes described, for example, in Aldrichimica Acta, vol. 40, No. 2, 2007, pp. 45-52.

Examples of such catalysts are Grubbs catalysts, Hoveyda-Grubbs catalysts, Piers-Grubbs catalysts, and other metathesis catalysts of the same type, whether they are "1st-generation", "2nd-generation" or "3rd-generation" catalysts.

Grubbs catalysts are based on a ruthenium atom surrounded by 5 ligands:
  2 anionic ligands, such as halides;
  2 electron-donating ligands, such as trialkylphosphines, or saturated N-heterocyclic carbenes (called NHC ligands);
  an alkylidene group, such as substituted or unsubstituted methylene groups $=CR_2$.

These metathesis catalysts are classified into two categories, depending on the nature of their electron-donating ligands L:
  those which contain two phosphine ligands (and no saturated NHC ligand), developed first, are 1st-generation catalysts;
  those which contain a saturated NHC ligand (a heterocyclic carbene) are 2nd-generation catalysts.

A type of catalyst known as a "Hoveyda-Grubbs" catalyst contains, among the electron-donating ligands, a benzylidene-ether chelating ligand, and either a phosphine (1st generation) or a saturated NHC ligand (2nd generation), usually substituted with phenyls generally substituted with mesityl (Mes) groups or else with isopropyl (iPr) groups.

Another type of catalyst termed "Piers-Grubbs" catalyst forms a four-ligand cationic complex which does not require dissociation of a ligand before the reaction.

Other types of catalysts are the "Umicore", "Zanan" and "Grela" catalysts.

Generally, the choice of the catalyst depends on the reaction under consideration.

Preferably, the catalyst used in the process of the invention is free of phosphine.

By way of example, catalysts that are particularly suitable for the process of the invention are the following catalysts:

(1) The catalyst denoted "Hoveyda-Grubbs 2", having the following formula:

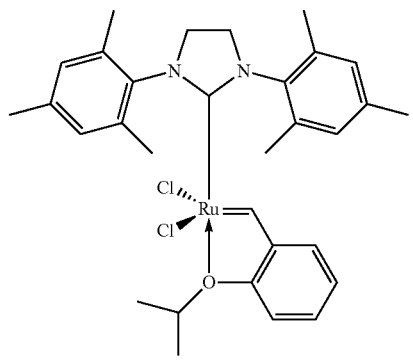

(2) The catalyst denoted "M51", having the following formula:

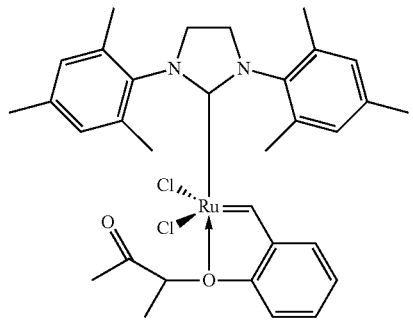

(3) The catalyst denoted "M71-SIPr", having the following formula:

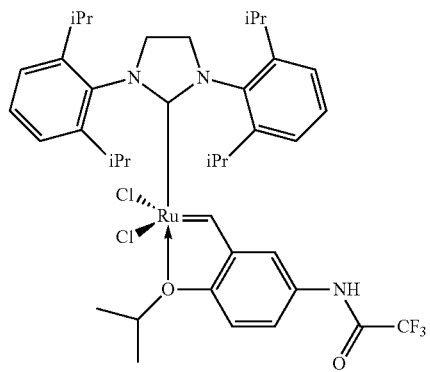

(4) The catalyst denoted "M71-SIMes", having the following formula:

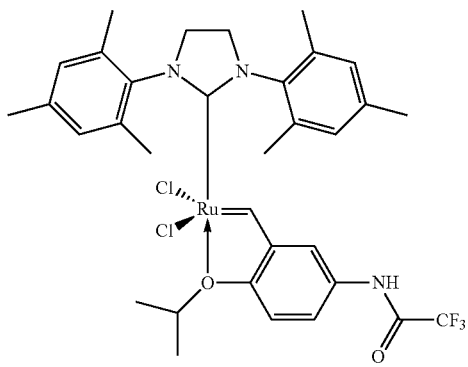

(5) The catalyst denoted "M72-SIPr", having the following formula:

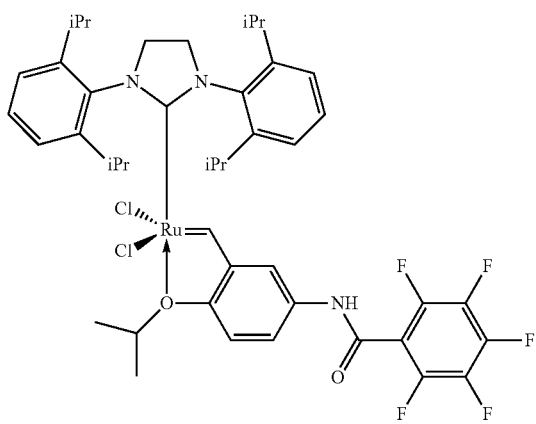

(6) The catalyst denoted "M73-SIPr", having the following formula:

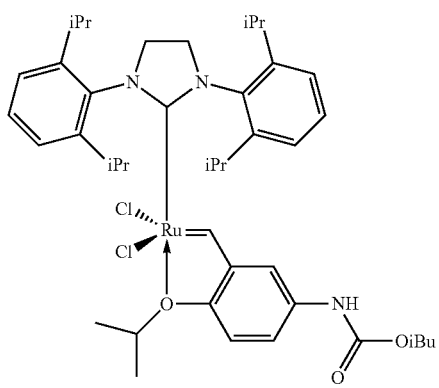

(7) The catalyst denoted "M74-SIPr", having the following formula:

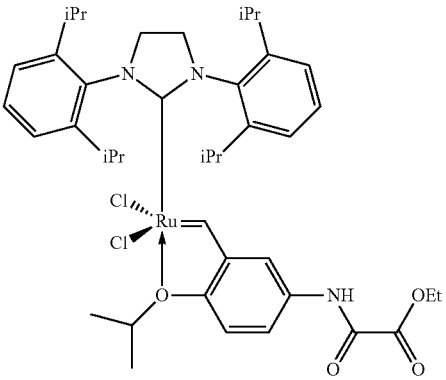

(8) The catalyst denoted "Nitro-Grela-SIMes", having the following formula:

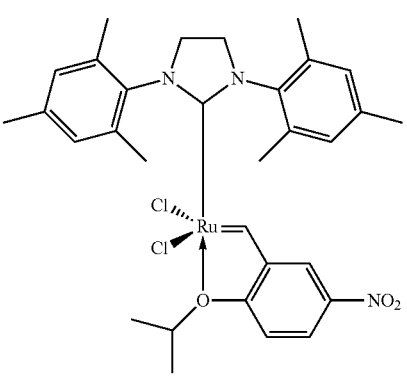

(9) The catalyst denoted "Nitro-Grela-SIPr", having the following formula:

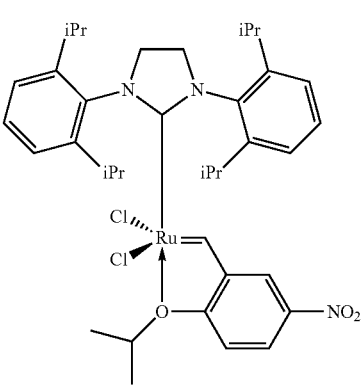

(10) The catalyst denoted "Apeiron AS2034", having the following formula:

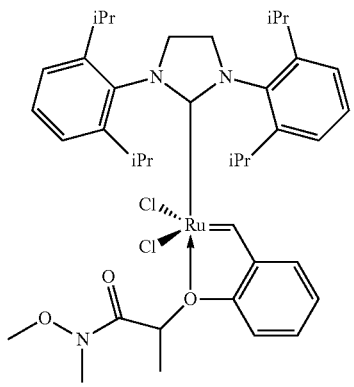

(11) The catalyst denoted "Zannan 44-0082 (Strem)", having the following formula:

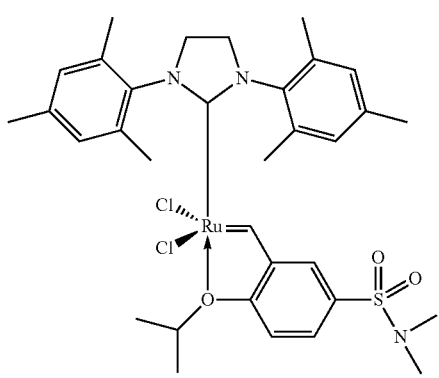

(12) The catalyst denoted "M831-SIPr", having the following formula:

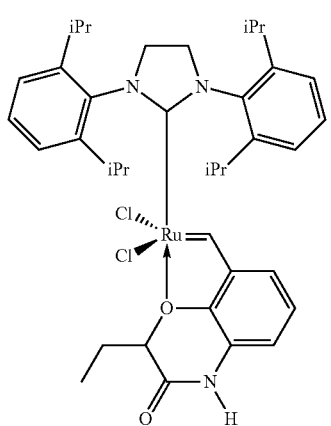

(13) The catalyst denoted "M832-SIPr", having the following formula:

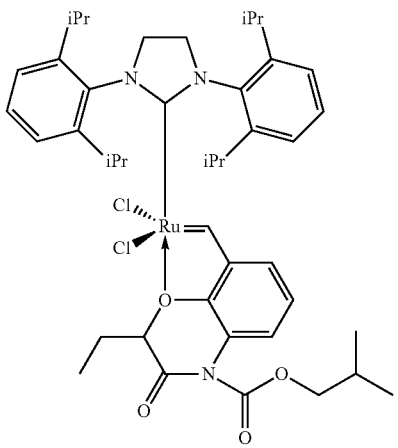

(14) The catalyst denoted "M853-SIPr", having the following formula:

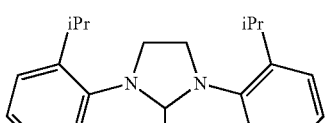

(15) The catalyst denoted "M863-SIPr", having the following formula:

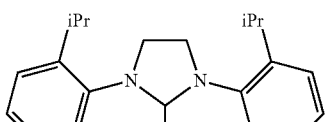

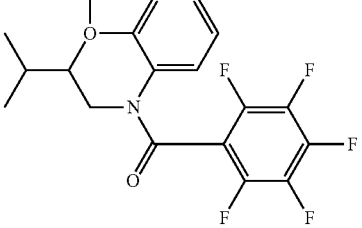

(16) The catalyst denoted "Materia C711", having the following formula:

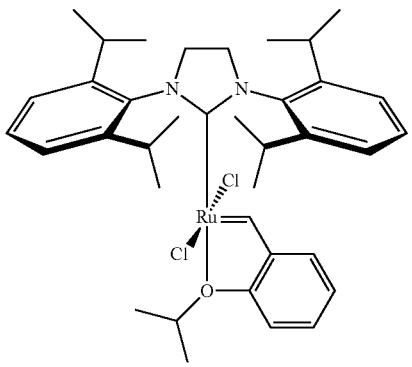

Preferably, the metathesis reaction is performed in liquid medium and under the following operating conditions.

The reaction temperature is generally in the range from 20 to 160° C. and preferably in the range from 20 to 120° C.

The reaction pressure is generally in the range from 1 to 30 bar. The reaction is preferably performed at low pressure in the range from 1 to 10 bar and more preferably at atmospheric pressure when the boiling point of the reagents used makes it possible. Specifically, if an evolution of a light olefin, whether it is ethylene or another, is always intended, it is advantageous to work at low pressure, preferably atmospheric pressure. However, constraints exist linked to the boiling point of the olefin used in the process of the invention which is performed in liquid phase. In the case where this boiling point is low, for example for a C5 olefin in which it is of the order of 20° C., it is necessary to work under pressure. This constraint disappears with the higher olefins. For example, a C7 olefin, whose boiling point is of the order of 80° C., makes it possible to work at atmospheric pressure.

The reaction may be performed without solvent or in the presence of a solvent such as toluene, xylenes or dichloromethane, for example. The reaction is preferably performed without solvent.

In a preferred embodiment of the process of the invention, the catalyst and/or the olefin (II) and/or the fatty molecule (compound I) are added continuously to the reaction medium during the reaction process.

The branched unsaturated fatty compound III derived from the cross metathesis reaction of the process of the invention may serve as starting material for an entire range of reactions. Nonlimiting examples that may be mentioned include the following reactions:

hydrogenation of said at least one double bond C═C (of compound III or derived from compound III), which leads, depending on the type of hydrogenation, for the esters, to saturated esters, saturated alcohols, or even branched paraffins, and, for the nitriles, to branched amines;

hydrolysis of ester, which leads to an acid;

nitrilation of acid or ester, depending on whether or not there is an intermediate hydrolysis, followed by optional conversion of the nitrile into amine by hydrogenation;

epoxidation of said at least one double bond C═C (of compound III or derived from compound III), with or without opening of the epoxy ring, to form diols, carbonates, esters, etc., leading to the epoxy of a branched chain, which gives improved viscosity properties. In this case, it is advantageous to work with polyunsaturated compounds;

new step of metathesis in particular in the case where the metathesis with the branched olefin was performed on a diester. In this case, the new metathesis makes it possible to recycle part of the reaction coproduct, which is a short ester, for example methyl decenoate or methyl undecenoate.

Depending on the intended applications, certain fatty chains are more suitable than others, which implies a selection of the plant oils, but also of the nature of the starting material used for the metathesis reaction, namely triglyceride, monoalcohol or polyalcohol ester, acid or nitrile.

The plant oils and animal fats may be regrouped according to their contents of saturated, monounsaturated and polyunsaturated fatty acids.

The oils rich in polyunsaturated fatty chains include safflower oil (high linoleic content), linseed oil, sunflower oil, walnut and hazelnut oil, soybean oil, cotton seed oil, corn oil, Jatropha oil, rapeseed oil and camelina oil.

The oils rich in saturated fatty chains are generally unsuitable for the metathesis reaction, which requires unsaturations in order for the reaction to be able to take place. However, these oils are generally cheap and nevertheless contain very few polyunsaturated chains, which affords the advantage of obtaining much more selective reactions. This group of plant oils includes palm oils, and animal fats such as beef fat and lard. On the other hand, babassu oil, coconut oil and palm kernel oil are not advantageous, not only on account of their lower content of unsaturations, but also of their much higher price.

The last group of plant oils consists of oils rich in monounsaturated chains, especially "oleic" oils. This is the case for rapeseed oils, especially oleic and high-oleic rapeseed (with a higher content of oleic acid), oleic sunflower oil, sea kale oil, erucic rapeseed oil, oleic safflower oil, honesty oil, olive oil, castor oil and lesquerella oil, especially fendleri, grandi flora and gordonii varieties.

According to a particular embodiment, the process of the invention also comprises a hydrogenation step for the synthesis of saturated branched fatty compounds, especially saturated esters, saturated alcohols, saturated nitriles, saturated amines and saturated fatty acids. In this case, compound I used is preferably a monounsaturated fatty ester, derived from oil(s) rich in monounsaturated fatty acids, or alternatively from fatty ester(s) which have already undergone a step of cross metathesis with a light olefin or a step of thermal cracking.

According to another embodiment, the process of the invention is used for synthesizing branched unsaturated fatty compounds used as lubricants. In this latter case, compound I (also known as the "fatty molecule") is preferably chosen from: triglycerides, especially triglycerides that have already undergone a metathesis step or monounsaturated fatty acid esters, especially w-unsaturated fatty acid esters.

According to yet another embodiment, the process of the invention is used for synthesizing branched unsaturated fatty compounds that need to undergo an epoxidation. In this case, compound I (or the fatty molecule) is advantageously chosen from triglycerides and esters derived from oils rich in polyunsaturated fatty acids.

According to another embodiment, the process of the invention is used for manufacturing dielectric fluids. In this case, compound I (or the fatty molecule) is advantageously chosen from triglycerides and esters derived from oils rich in monounsaturated fatty acids and preferably containing an unsaturation in position delta-5 to delta-9.

Preferably, the product obtained according to the process of the invention is at least partially hydrogenated, so as to increase the stability of the formulations comprising it.

A subject of the present invention is also the use of the product obtained according to the process of the invention for manufacturing at least one of the following products: dielectric fluids, specialty surfactants, emulsifiers, friction agents, antistatic additives, antifogging additives, mold-release agents, pigment dispersants, high-performance lubricants, waxes and wax emulsifiers, polymer transformation additives, PVC stabilizers, inks, resins, paints, varnishes, solvents, lipsticks, skin creams, deodorants, especially in stick form, hair dyes, shampoos and other liquid soaps, shaving foams, detergents, cleaning agents, textile softeners, and mixtures thereof. More generally, the product obtained according to the process of the invention may be used in any application that is stringent in terms of purity, low melting point and stability (or resistance) to oxidation.

EXAMPLES

The examples that follow illustrate the invention without limiting it.

Example 1

The test is performed in the following experimental device.

The device is composed of a 600 ml round-bottomed flask equipped with a nitrogen inlet, a temperature probe, a cooler (on which is mounted a tap and which exits to a bubbler), an oil bath and an inlet for the reagents, and a syringe pump bearing syringes for injecting the olefin and the catalyst, which are added continuously.

The assembly is first purged with nitrogen, the supply of which will be stopped at the time of loading of the olefin and the catalyst.

The catalyst M71SiPr from Umicore is prepared as follows: 10.2 mg, weighed out in a glass crucible, are dissolved in 21.6 g of toluene in a Schlenk tube under nitrogen. 5 ml of this solution, i.e. 2.02 mg of catalyst, are introduced into a first syringe.

A second syringe is prepared, into which are placed 4.4 g of 5-methyl-1-hexene (molar mass: 98 g/mol), i.e. 44 mmol.

The reactor is loaded with 150 g of toluene and then with 15 g of methyl 10-undecenoate (molar mass 198 g/mol), i.e. 76 mmol purified by adsorption, 1 g of dodecane (used as internal calibration) and finally with 4.4 g of olefin(5-methyl-1-hexene), i.e. again 44 mmol.

The mixture is heated to 110° C. while leaving the cooler tap open, and the temperature of the medium is controlled, (oil bath at 145° C.)

A first sample is collected at t=0 and the start of the reaction (t=0) is initiated, and the catalyst and the olefin (44 mmol prepared above) are added continuously over 2 hours at a flow rate of 22 mmol/hour for the olefin. A sample is collected at t=120 min and GC analysis is performed on the samples. At the end of the reaction, the heating is stopped, the cooler bath and the mixture is left to cool.

The GC analysis conditions are: HP5 column of 30 m×0.32 mm, thickness 0.25 μm, Injector T=300° C., FID detector T=340° C., Column 150° C. for 5 minutes, then 10° C./min up to 320° C., then 30 min at 320° C.

The conversion of the methyl undecenoate is 85% and the yield of branched unsaturated fatty compound (cross metathesis product) methyl 14-methyl-pentadec-10-enoate is 71%.

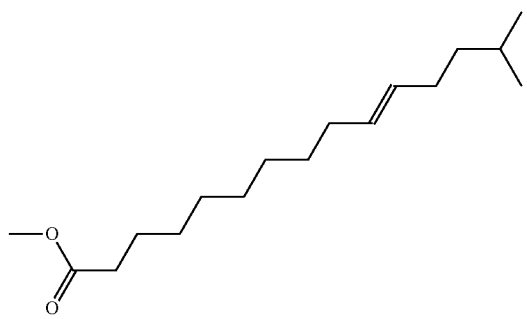 [SMILES: COC(=O)CCCCCCCC/C=C/CCC(C)C]

Example 2

Cross Metathesis of Methyl Decenoate+Neohexene

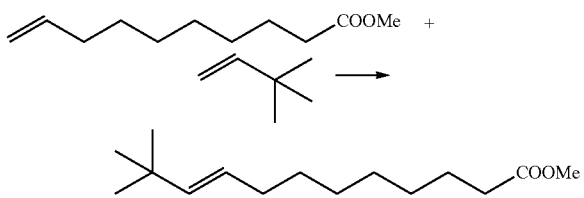

10 g of methyl 9-decenoate (54 mmol) purified on alumina, 18.1 g of 3,3-dimethyl-1-butene (neohexene, 215 mmol, 4 equivalents) and 100 g of toluene are placed in a 250 ml 10 glass reactor purged with nitrogen. The mixture is heated at 40° C., followed by addition, over a period of 2 hours, of 3.4 mg of catalyst M73-SiPr supplied by the company Umicore (75 ppm mol) dissolved in 5 ml of toluene. At the end of the addition, the degree of conversion of the methyl decenoate, measured by CPG, is 86%. The selectivity toward cross metathesis product is 35%.

25. The process of claim 11, wherein said catalyst Is of formula:
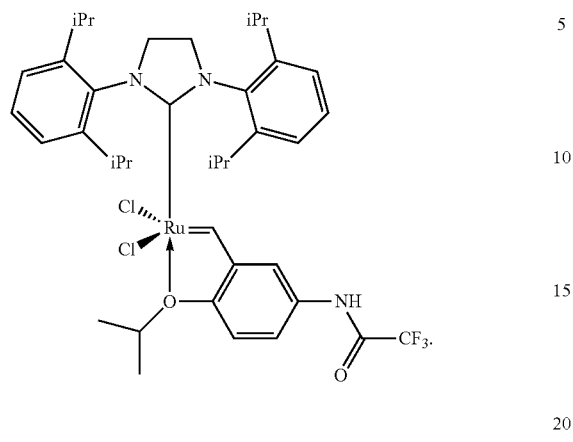

The invention claimed is:

1. A process for synthesizing a branched unsaturated fatty compound of formula III: A-CH=CB'—B wherein:
   A is a radical consisting of an linear alkyl chain, comprising from 1 to 20 carbon atoms and comprising an acid, ester of a monoalcohol or of a polyol or nitrile end function;
   B' is H or an alkyl chain comprising from 1 to 10 carbon atoms; and
   B is:
   if B' is an alkyl chain, B is an alkyl chain comprising from 1 to 11 carbon atoms; and
   if B' is H, B is an alkyl chain comprising from 3 to 11 carbon atoms bearing at least one branched alkyl radical of formula $C_nH_{2n+1}$ with n in the range from 1 to 5, said process comprising:
   performing metathesis in the presence of a metathesis catalyst between:
   (a) a linear unsaturated fatty compound of formula I R—$(CH_2)_a$-[(CH=CH)—$(CH_2)_b$]—$(CH_2)_c$—R' is wherein R' is a radical —COOH, $COOR_1$ or —CN, $R_1$ being a monoalcohol or a polyol residue R is H or an acid, monoalcohol ester or nitrile function, and a, b, c are integers such that 0≤a≤11; 1≤b≤6; 2≤c≤12, the sum a+3*b+c+1 being in the range from 8 to 36; and (b) a branched olefin II comprising from 4 to 23 carbon atoms, wherein the main chain comprises at least one branching of formula $C_nH_{2n+1}$ with n in the range from 1 to 5 when B' is H.

2. The process as claimed in claim 1, wherein the linear unsaturated fatty compound I is chosen from: monounsaturated or polyunsaturated fatty acids or fatty acid esters, Including mono-, di- and triglycerides, and nitrile derivatives, of the following fatty acids: oleic, petroselinic, linoleic, ricinoleic, gadoleic, gondoic, vaccenic, linolenic, palmitoleic, erucic, nervonic, and mixtures thereof.

3. The process of claim 1, wherein compound I is chosen from:
   nitrile derivatives obtained by nitridation of an ester or acid function of a fatty ester or fatty acid;
   difunctional molecules bearing acid, ester or nitrile functions at each end of the molecule;
   triglycerides; and
   functional molecules comprising from 8 to 12 carbon atoms.

4. The process of claim 1, wherein the branched olefin II used for the metathesis reaction contains at least 5 carbon atoms in total.

5. The process of claim 1, wherein the branched olefin II is of formula II: $R_0R_0'C$=$CBB'$ wherein:
   B' is H or an alkyl chain comprising from 1 to 10 carbon atoms, and
      if B' Is an alkyl chain, B is an alkyl chain comprising from 1 to 11 carbon atoms, and
      if B' is H, B is an alkyl chain comprising from 3 to 11 carbon atoms including at least one carbon atom bearing an alkyl radical of formula $C_nH_{2n+1}$ with n in the range from 1 to 5, and
   $R'_0$ is H or an alkyl chain comprising from 1 to 10 carbon atoms, and
      if $R'_0$ is H, $R_0$ is H, $CH_3$, $C_2H$ or an alkyl chain comprising from 3 to 11 carbon atoms Including at least one carbon atom bearing an alkyl radical of formula $CH_{2n+1}$ with n in the range from 1 to 5, and
      if $R'_0$ is an alkyl chain, $R_0$ s H or an alkyl chain comprising from 1 to 11 carbon atoms.

6. The process as claimed in claim 5, wherein, in formula II of the olefin, B' is H and B is of formula —$(CR_2R)_m$—$CH_3$ wherein $R_2$ and $R_3$, which may be identical or different, are either H or a saturated alkyl radical comprising from 1 to 5 carbon atoms, the radicals $R_2$, on the one hand, and the radicals $R_3$, on the other hand, linked to the carbon atoms of the chain being identical to or different from each other, and at least one of the radicals $R_2$ and $R_3$ being a saturated alkyl radical.

7. The process of claim 1, wherein said at least one branching of the olefin is located closer to the double bond C=C than the end of the chain which bears said branching.

8. The process of claim 7, wherein each carbon atom of the double bond of formula II: $R_0R_0'C$=$CBB'$ bears only one alkyl chain.

9. The process of claim 1, wherein the carbon atoms of said at least one double bond of the olefin are linked on one side of the double bond to a chain of not more than 2 other carbon atoms.

10. The process of claim 1, wherein the metathesis catalyst comprises at least one ruthenium-carbene catalyst chosen from the charged or uncharged catalysts of general formula:

$$(X_1)_a(X_2)_b\text{Ru}(\text{carbene C})(L_1)_c(L_2)_d(L_3)_e$$

wherein:
   a, b, c, d and e are Integers, which may be Identical or different, with a and b equal to 0, 1 or 2; c, d and e equal to 0, 1, 2, 3 or 4;
   $X_1$ and $X_2$, which may be identical or different, each represent a charged or uncharged and monochelating or polychelating ligand; and
   $L_1$, $L_2$ and $L_3$, which may be identical or different, are electron-donating ligands.

11. The process as claimed in claim 10, wherein the catalyst comprises a saturated NHC ligand substituted with phenyls substituted with mesityl (Mes) or Isopropyl (iPr) groups.

12. The process of claim 1, wherein the process is performed in liquid medium at a temperature in the range from 20 to 160° C. and at a pressure in the range from 1 to 30 bar.

13. The process as claimed in claim 8, wherein the process is performed at a temperature in the range from 20 to 120° C. and at a pressure in the range from 1 to 10 bar.

14. The process of claim 1, wherein the reaction Is performed in the presence of a solvent.

15. The process of claim 1, further comprising:
   after the production of compound III bearing at least one double bond C=C, at least one of the following reactions
   hydrogenation of said at least one double bond C=C, which leads, depending on the type of hydrogenation, for the esters, to saturated esters, saturated alcohols, or even branched paraffins, and, for the nitriles, to branched amines;
   hydrolysis of ester, which leads to an acid;
   nitration of acid or ester, depending on whether or not there Is an Intermediate hydrolysis;
   epoxidation of said at least one double bond C=C, with or without opening of the epoxy ring to form diols, carbonates or esters, leading to the epoxy of a branched chain; and/or
   new step of metatheses.

16. The process of claim 1, further comprising:
   a step of hydrogenation for the synthesis of saturated branched fatty compounds.

17. The process of claim 1, further comprising an epoxidation of compound III, compound I being chosen from triglycerides and esters derived from oils rich in polyunsaturated fatty acids.

18. The process of claim 1, wherein the linear alkyl chain of A is unsaturated.

19. The process of claim 1, wherein the alkyl chain of B is branched, when B' is an alkyl chain.

20. The process of claim 4, wherein said branch olefin II used for the metathesis reaction comprises from 7 to 12 carbon atoms in total.

21. The process of claim 5, wherein the alkyl chain of B is branched, when B' is an alkyl chain.

22. The process of claim 5, wherein the alkyl chain of $R_0$ is branched, when $R'_0$ is an alkyl chain.

23. The process of claim 5, wherein each carbon atom of the double bond of formula II: $R_0R'_0C$=$CBB'$ bears only one alkyl chain.

24. The process of claim 9, wherein said carbon atoms are of the 1-alkene, 2-alkene, or 3-alene type.